US008038943B2

(12) United States Patent
Yoo et al.

(10) Patent No.: US 8,038,943 B2
(45) Date of Patent: Oct. 18, 2011

(54) METHOD OF DETECTING BIO-MOLECULES USING FIELD EFFECT TRANSISTOR WITHOUT FIXING PROBE BIO-MOLECULES ON THE GATE SENSING SURFACE

(75) Inventors: Kyu-tae Yoo, Yongin-si (KR); Kyu-sang Lee, Yongin-si (KR); Won-seok Chung, Yongin-si (KR); Jeo-young Shim, Yongin-si (KR); Yeon-ja Cho, Yongin-si (KR)

(73) Assignee: Samsung Electronics Co., Ltd. (KR)

( * ) Notice: Subject to any disclaimer, the term of this patent is extended or adjusted under 35 U.S.C. 154(b) by 933 days.

(21) Appl. No.: 11/695,905

(22) Filed: Apr. 3, 2007

(65) Prior Publication Data
US 2009/0322354 A1    Dec. 31, 2009

(30) Foreign Application Priority Data

Apr. 3, 2006    (KR) .................. 10-2006-0030170

(51) Int. Cl.
*G01N 27/00* (2006.01)
(52) U.S. Cl. ............... 422/82.01; 435/283.1; 435/287.1; 435/287.3; 422/50; 422/68.1
(58) Field of Classification Search ............... 435/283.1, 435/287.1, 287.3; 422/50, 68.1, 82.01
See application file for complete search history.

(56) References Cited

U.S. PATENT DOCUMENTS

| | | | |
|---|---|---|---|
| 4,238,757 A | 12/1980 | Schenck | |
| 4,777,019 A | 10/1988 | Dandekar | |
| 4,874,499 A * | 10/1989 | Smith et al. | ............. 204/403.03 |
| 5,466,348 A | 11/1995 | Holm-Kennedy | |
| 5,846,708 A | 12/1998 | Hollis et al. | |
| 6,203,981 B1 | 3/2001 | Ackley et al. | |
| 7,303,875 B1 * | 12/2007 | Bock et al. | ........................ 435/6 |
| 2004/0134798 A1 * | 7/2004 | Toumazou et al. | ........ 205/793.5 |
| 2005/0179065 A1 | 8/2005 | Chou et al. | |
| 2005/0212016 A1 * | 9/2005 | Brunner et al. | ............... 257/253 |
| 2006/0011911 A1 * | 1/2006 | Bockelmann et al. | .......... 257/48 |

FOREIGN PATENT DOCUMENTS

| | | |
|---|---|---|
| WO | 0201647 | 1/2002 |
| WO | 02086162 | 10/2002 |
| WO | WO03062811 | 7/2003 |
| WO | 2005043160 | 5/2005 |

OTHER PUBLICATIONS

Sakurai, et al., Real-Time Monitoring of DNA Polymerase Reactions by a Micro ISFET pH Sensor, Department of Environmental Chemistry, Saitama University, Urawa 338, Japan, Anal. Chem. 1992, 64, 1996-1997, XP009015113.

* cited by examiner

*Primary Examiner* — Melanie J Yu
(74) *Attorney, Agent, or Firm* — Cantor Colburn LLP

(57) ABSTRACT

A method of detecting a presence of bio-molecules, or a concentration of the target bio-molecules using a field effect transistor, includes allowing a first sample including a first target bio-molecule to contact a sensing surface of the field effect transistor and measuring a change in an electric signal of the field effect transistor, the field effect transistor including a substrate, a source region and a drain region, the source region and the drain region formed apart from each other on the substrate, the source region and the drain region each doped to having an opposite polarity than a polarity of the substrate, a channel region disposed between the source region and the drain region and an insulating layer including the sensing surface, the insulating layer disposed on the channel region.

16 Claims, 3 Drawing Sheets

METHOD OF DETECTING BIO-MOLECULES USING FIELD EFFECT TRANSISTOR WITHOUT FIXING PROBE BIO-MOLECULES ON THE GATE SENSING SURFACE

This application claims priority to Korean Patent Application No. 10-2006-0030170, filed on Apr. 3, 2006, and all the benefits accruing therefrom under 35 U.S.C. §119, the contents of which in its entirety are herein incorporated by reference.

BACKGROUND OF THE INVENTION

1. Field of the Invention

The present invention relates to a method of detecting the presence of target bio-molecules or a concentration of the target bio-molecules using a field effect transistor, and more particularly to a method of detecting the presence of the target bio-molecules or the concentration of the target bio-molecules using the field effect transistor without fixing a probe bio-molecule on a gate sensing surface of the field effect transistor.

2. Description of the Related Art

A transistor based bio-sensor which includes a transistor is one type of sensor which detects bio-molecules using electric signals. Since a semiconductor is used to manufacture the transistor based bio-sensor, the cost of manufacture and the amount of time required to detect the bio-molecules using the electric signals are reduced. Accordingly, much research on this type of sensor has been carried out.

U.S. Pat. No. 4,238,757 discloses a field effect transistor ("FET") which can be used to detect biological reactions. Using the FET, a bio-sensor measures a change in current of an inversion layer of a semiconductor resulting from changes in the surface charge concentration in order to detect an antigen-antibody reaction. Employing a bio-sensor using the FET, a protein among bio-molecules can be detected. U.S. Pat. No. 4,777,019 discloses a sensor for measuring hybridization of biological monomers with complementary monomers by adsorbing the biological monomers onto a surface of a gate using a FET.

U.S. Pat. No. 5,846,708 discloses a method of determining a presence of hybridization by an extinction of coupled bio-molecules using a charged couple device ("CCD"). U.S. Pat. Nos. 5,466,348 and 6,203,981 disclose a method of increasing signal to noise ratio ("SNR") using a thin film transistor ("TFT") with a circuit.

The use of the FET as a bio-sensor decreases costs and reduces the amount of time required to detect the bio-molecules, and the FET is easily used together with an integrated circuit/microelectromechanical system ("IC")/("MEMS").

FIG. 1A is a schematic front view illustration of a structure of a conventional FET sensor of the prior art. Referring to FIG. 1A, the FET includes a substrate 11 doped with an n-type or a p-type material, a source 12a and a drain 12b which are formed apart from each other on two sides of the substrate 11 and the source 12a and the drain 12b are each doped having an opposite polarity to the substrate 11 and a gate 13 formed on the substrate 11 which contacts the source 12a and the drain 12b. Generally, the gate 13 includes an oxide layer 14, a poly silicon layer 15 and a gate electrode 16. A channel is generally formed between the source 12a and the drain 12b. Probe bio-molecules 18 are adhered to the sensing surface of the gate electrode 16 which faces a reference electrode 17. The probe bio-molecule 18 binds to a target bio-molecule (not shown) through a hydrogen bond, or the like, and the bond is detected using an electrical method.

FIG. 1B is a schematic front view illustration of a process of immobilizing probe bio-molecules 18 on the surface of a gate electrode 16 of the FET illustrated in FIG. 1A and binding target bio-molecules (not shown) with the probe bio-molecules 18. Referring to FIG. 1B, a current flowing through a channel varies according to the presence of the immobilized probe bio-molecules 18 on the surface of the gate electrode 16 and the presence of the bond between immobilized probe bio-molecules 18 and the target bio-molecules (not shown), and thus the target bio-molecules can be detected by measuring a variance in the current flowing through the channel.

In all conventional FET structures, probe bio-molecules such as an oligonucleotide or a polymerase chain reaction ("PCR") product are immobilized on the surface of a gate electrode. An immobilizing technology is used to manufacture a microarray or a modified technology is used to immobilize the bio-molecules. In International Publication No. WO 03/062811, for example, a surface of a gate is treated with a poly-L-lysine ("PLL") having a positive charge using a wet process, deoxyribonucleic acid ("DNA") is spotted on the surface of the gate using a spotter and a voltage is measured before and after the spotting.

However, a FET including probe bio-molecules immobilized on the surface of a gate should be disposed of after use and a response time of the sensor is not fast enough. Further, an additional process, such as a coating or depositing an additional layer, is required to immobilize the probe bio-molecules. However, it is expected that this additional processing will vary characteristic properties between the FETs. In addition, it is difficult to use spotting to immobilize the probe bio-molecules on a lab-on-a-chip ("LOC").

BRIEF SUMMARY OF THE INVENTION

The present invention provides a method of continuously, easily and accurately detecting the presence of target bio-molecules and a concentration of the target bio-molecules.

According to an exemplary embodiment of the present invention, there is provided a method of detecting a presence of target bio-molecules or a concentration of the target bio-molecules using a field effect transistor, the method includes allowing a first sample including a first target bio-molecule to contact a sensing surface of the field effect transistor and measuring a change in an electric signal of the field effect transistor, the field effect transistor including a substrate, a source region and a drain region, the source region and the drain region formed apart from each other on the substrate, the source region and the drain region each doped having an opposite polarity than a polarity of the substrate, a channel region disposed between the source region and the drain region and an insulating layer including the sensing surface, the insulating layer disposed on the channel region.

In the exemplary embodiment, the substrate of the field effect transistor may be formed of a semiconductor material.

In the exemplary embodiment, the insulating layer may be composed of an electrically insulating material.

In the exemplary embodiment of the present invention, the method may further include allowing a second sample including a second target bio-molecule to contact the sensing surface of the field effect transistor.

The exemplary embodiment of the method may further include washing the sensing surface of the field effect transistor with a solution which lacks bio-molecules before allowing the second sample including the second target bio-molecule to contact the sensing surface of the field effect transistor.

The electric signal may include at least one of a drain current, a gate-source voltage and a source-drain voltage.

The bio-molecules may be a nucleic acid or a protein.

The nucleic acid may be one of deoxyribonucleic acid ("DNA"), ribonucleic acid ("RNA"), peptide nucleic acid ("PNA"), locked nucleic acid ("LNA") and a hybrid thereof.

The protein may be one of an enzyme, a substrate, an antigen, an antibody, a ligand, an aptamer and a receptor.

The nucleic acid may be a polymerase chain reaction ("PCR") product or a purified PCR product.

The substrate may be silicon and the electrically insulating material may be one of a silicon dioxide, a silicon nitride and a metal oxide.

The substrate may be doped with an n-type material and the source region and the drain region each may be doped with a p-type material.

The substrate may also be doped with a p-type material and the source region and the drain region each may be doped with an n-type material.

The field effect transistor may be in fluid communication with a microchannel.

The field effect transistor may be at least partially formed in a microchannel.

An inner wall of the microchannel may be composed of the substrate.

BRIEF DESCRIPTION OF THE DRAWINGS

The above and other aspects, features and advantages of the present invention will become more apparent by describing in more detail exemplary embodiments thereof with reference to the accompanying drawings in which.

DETAILED DESCRIPTION OF THE INVENTION

Figure 1A:
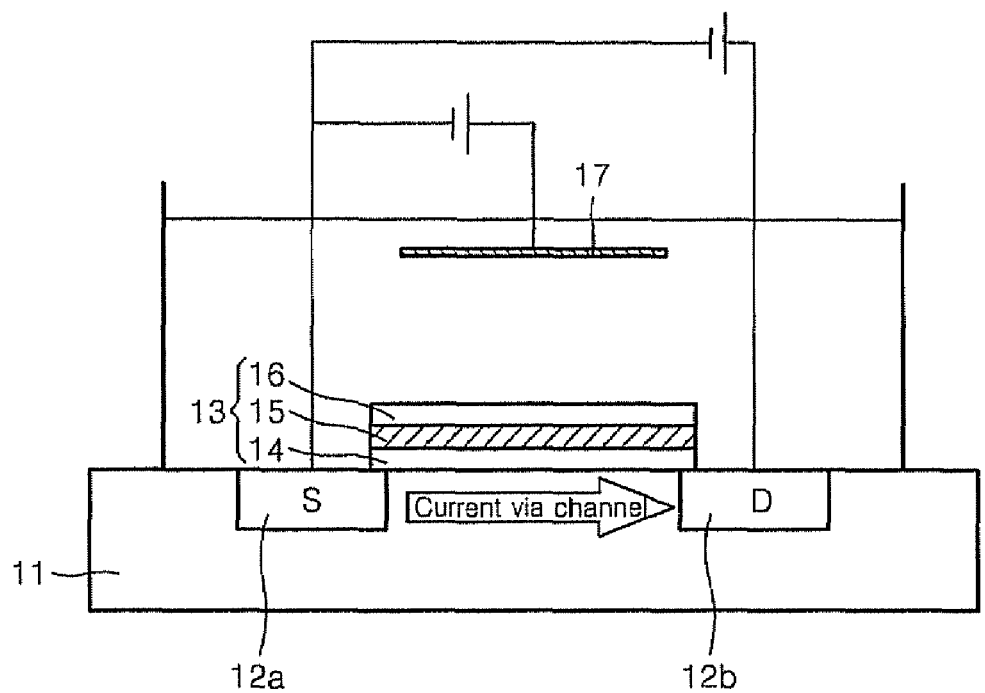
FIG. 1A is a schematic front view illustration of a structure of a conventional field effect transistor sensor of the prior art.
Figure 1B:
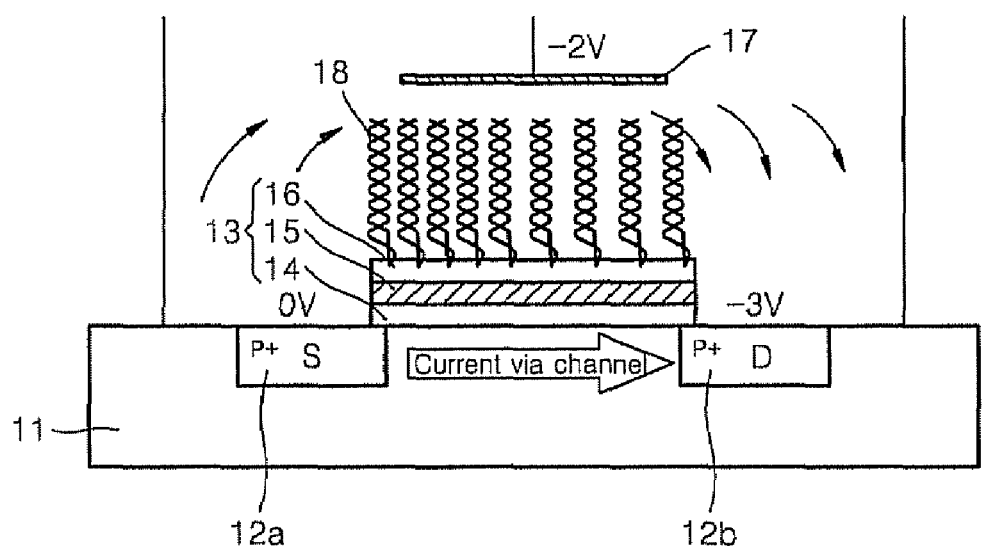
FIG. 1B is a schematic front view illustration of a process of immobilizing probe bio-molecules on a surface of a gate electrode of the field effect transistor illustrated in FIG. 1A and binding target bio-molecules with probe bio-molecules of the prior art.

The invention now will be described more fully hereinafter with reference to the accompanying drawings, in which embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art. Like reference numerals refer to like elements throughout.

It will be understood that when an element is referred to as being "on" another element, it can be directly on the other element or intervening elements may be present therebetween. In contrast, when an element is referred to as being "directly on" another element, there are no intervening elements present. As used herein, the term "and/or" includes any and all combinations of one or more of the associated listed items.

It will be understood that, although the terms first, second, third etc. may be used herein to describe various elements, components, regions, layers and/or sections, these elements, components, regions, layers and/or sections should not be limited by these terms. These terms are only used to distinguish one element, component, region, layer or section from another element, component, region, layer or section. Thus, a first element, component, region, layer or section discussed below could be termed a second element, component, region, layer or section without departing from the teachings of the present invention.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

Furthermore, relative terms, such as "lower" or "bottom" and "upper" or "top," may be used herein to describe one element's relationship to another elements as illustrated in the Figures. It will be understood that relative terms are intended to encompass different orientations of the device in addition to the orientation depicted in the Figures. For example, if the device in one of the figures is turned over, elements described as being on the "lower" side of other elements would then be oriented on "upper" sides of the other elements. The exemplary term "lower", can therefore, encompasses both an orientation of "lower" and "upper," depending of the particular orientation of the figure. Similarly, if the device in one of the figures is turned over, elements described as "below" or "beneath" other elements would then be oriented "above" the other elements. The exemplary terms "below" or "beneath" can, therefore, encompass both an orientation of above and below.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

Exemplary embodiments of the present invention are described herein with reference to cross section illustrations that are schematic illustrations of idealized embodiments of the present invention. As such, variations from the shapes of the illustrations as a result, for example, of manufacturing techniques and/or tolerances, are to be expected. Thus, embodiments of the present invention should not be construed as limited to the particular shapes of regions illustrated herein but are to include deviations in shapes that result, for example, from manufacturing. For example, a region illustrated or described as flat may, typically, have rough and/or nonlinear features. Moreover, sharp angles that are illustrated may be rounded. Thus, the regions illustrated in the figures are schematic in nature and their shapes are not intended to illustrate the precise shape of a region and are not intended to limit the scope of the present invention.

Hereinafter, the present invention will now be described in detail with reference to the accompanying drawings.

A presence of bio-molecules or a concentration of the bio-molecules can be detected using a field effect transistor according to an exemplary embodiment of the present invention without fixing bio-molecules to a gate electrode of the field effect transistor.

Figure 2:
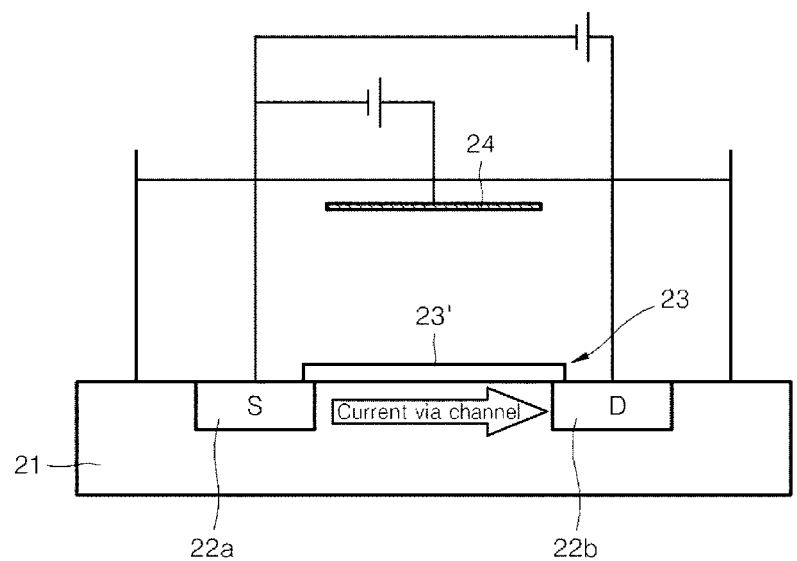
FIG. 2 is a schematic front view illustration of a structure of a field effect transistor used in a method of detecting bio-molecules of an exemplary embodiment of the present invention.

FIG. 2 is a schematic front view illustration of a structure of a field effect transistor for use in a method of detecting bio-molecules according to an exemplary embodiment of the present invention.

Referring to FIG. 2, the field effect transistor ("FET") for use in the exemplary method of detecting bio-molecules includes a substrate 21 composed of a semiconductor material, a source region 22a and a drain region 22b, the source region 22a and the drain region 22b are formed apart from each other on the substrate 21 and are each doped to include an opposite polarity to a polarity of the substrate 21, a channel region disposed between the source region 22a and the drain region 22b, an insulating layer 23 including a sensing surface 23' which is disposed at least partially on the channel region and the insulating layer 23 is composed of an electrically insulating material and a reference electrode 24 which is disposed apart from the insulating layer 23.

The field effect transistor for use in an exemplary embodiment of the present invention may be any field effect transistor which is commonly used in a conventional bio-sensor or in a complementary metal oxide semiconductor ("CMOS"). In exemplary embodiments, the field effect transistor may be a n-metal oxide semiconductor ("n-MOS") or a p-metal oxide semiconductor ("p-MOS"). In an exemplary embodiment, the substrate 21 is doped with an n-type material and the source region 22a and the drain region 22b are each doped with a p-type material. In an alternative exemplary embodiment, the substrate 21 is doped with a p-type material and the source region 22a and the drain region 22b are each doped with an n-type material.

In exemplary embodiments of the field effect transistor, the source region 22a may supply carriers such as free electrons or holes, and the drain region 22b may be a region to which the carriers supplied by the source region 22a reaches or travels toward, and the gate electrode 24 may control the flow of the carriers between the source region 22a and the drain region 22b.

Exemplary embodiments of the semiconductor constituting the substrate 21 may be silicon. Exemplary embodiments of the electrically insulating material constituting the insulating layer 23 may be any material on which bio-molecules do not become fixed, such as a silicon dioxide, a silicon nitride and a metal oxide. In alternative exemplary embodiments, an additional layer composed of a separate material on which bio-molecules do not become fixed may further be formed on the insulating layer 23.

In exemplary embodiments, the field effect transistor may be formed in or on at least a portion of a microchannel. In further exemplary embodiments, the substrate 21 may be included in or on at least a portion of an inner wall of the microchannel, and the gate electrode 24 may be disposed in or on at least a portion of the microchannel or on at least a portion of an inner wall of the microchannel.

In the method of detecting bio-molecules according to an exemplary embodiment of the present invention, the bio-molecules can be detected using the field effect transistor without fixing bio-molecules to the gate electrode 24 of the field effect transistor.

First, a first sample including a first target bio-molecule is provided to directly contact a gate electrode of the field effect transistor.

In an exemplary embodiment, the bio-molecule may be a nucleic acid or a protein.

The "nucleic acid" is meant to represent various nucleic acids, nucleic acid analogues and hybrids thereof. For example, the nucleic acid may be one of a deoxyribonucleic acid ("DNA"), a ribonucleic acid ("RNA"), a peptide nucleic acid ("PNA"), a locked nucleic acid ("LNA") and a hybrid thereof. In exemplary embodiments, the nucleic acid may be an oligonucleotide or a polymerase chain reaction ("PCR") product, and preferably a PCR product or a purified PCR product. However, the current invention is not limited to the introduction of thereof examples of bio-molecules or materials to the gate electrode of the field effect transistor.

Exemplary embodiments of the protein may be one of an enzyme, a substrate, an antigen, an antibody, a ligand, an aptamer and a receptor.

Next, in an exemplary embodiment of the current method, the gate electrode of the field effect transistor may be washed by providing a solution which lacks bio-molecules to the gate electrode after the first sample is provided to the gate electrode. In an exemplary embodiment, the solution may be an electrolyte solution.

Then, in further exemplary embodiments of the current method, a second sample including a second target bio-molecule may be provided to directly contact the gate electrode of the field effect transistor. In the exemplary embodiment, a concentration of the second target bio-molecule may be substantially similar to or substantially different from a concentration of the first target bio-molecule.

Changes in electric signal of the field effect transistor are measured during the process of providing samples including bio-molecules and a solution which lacks bio-molecules to the gate electrode.

In exemplary embodiments, the electric signal may include at least one of a drain current, a gate-source voltage and a source-drain voltage.

The method of detecting bio-molecules according to an exemplary embodiment of the present invention may be used to detect a corresponding PCR product of a bio-molecule to be detected. A PCR would occur if there are target bio-molecules present in the sample, but the PCR would not occur if there are no target bio-molecules in the sample. The presence of target bio-molecules and the concentration of the bio-molecules in the sample can be detected by detecting a corresponding PCR product using the current exemplary method according to the present invention.

In a method of detecting bio-molecules according to an exemplary embodiment of the present invention, various bio-molecules can be continuously detected, and the field effect transistor can be used continuously and is not required to be disposed of after each use. The target bio-molecules can be quickly detected using the field effect transistor in an exemplary method according to the present invention. In addition, since probe bio-molecules are not fixed on the field effect transistor, the field effect transistor can be simply manufactured and the variance of properties between a plurality of field effect transistors caused by additional processing can be effectively reduced, and thus the bio-molecules can be accurately detected.

Hereinafter, the present invention will be described in further detail with reference to the following examples. The following examples are for illustrative purposes and are not intended to limit the scope of the present invention.

Example 1

Preparation of a Field Effect Transistor Based Bio-Sensor

A field effect transistor device was fabricated using a XC10-1.0 μm CMOS process from X-FAB Semiconductor Foundry service (Germany). An upper surface of a gate was etched to expose silicon oxide, and a gate electrode was formed to be separate from the surface to prepare a field effect transistor as illustrated in FIG. 2.

Then, the surface of the field effect transistor including the exposed silicon oxide and the gate electrode was carefully washed with pure acetone and deionized water, and then dried. A wet station which is used in a semiconductor manufacturing process was used in washing the substrate. The substrate was then dried using a spin dry method.

Example 2

Detection of PCR Products Using the Field Effect Transistor Based Bio-Sensor It was determined whether a field effect transistor based bio-sensor manufactured in Example 1 could detect a PCR product without fixing the PCR product on an insulating layer in which the surface of the insulating layer senses the PCR product. It was also determined whether the field effect transistor based bio-sensor could detect another PCR product after washing off the previously detected PCR product.

For this example, PCR products and a washing solution were alternately provided to the field effect transistor based bio-sensor.

Figure 3A:
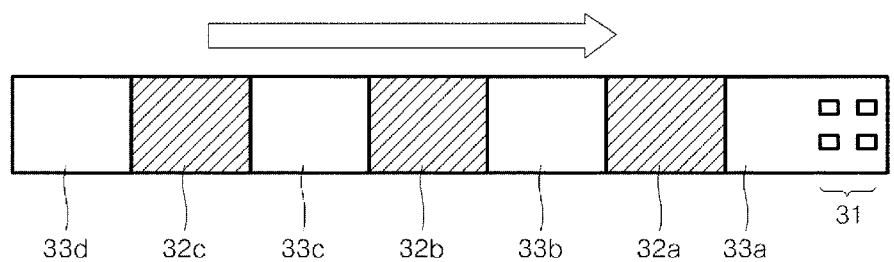
FIG. 3A is a schematic top view illustration of a procedure of alternately providing PCR products and a washing buffer to a gate electrode of the field effect transistor according to an exemplary embodiment of the present invention.

FIG. 3A is a schematic top view illustration of a procedure of alternately providing PCR products and a washing buffer to the gate electrode of the field effect transistor according to an exemplary embodiment of the present invention. Referring to FIG. 3A, a washing solution 33a, a PCR product 32a, a washing solution 33b, a PCR product 32b, a washing solution 33c, a PCR product 32c and a washing solution 33d were sequentially provided to at least one field effect transistor based bio-sensor 31 in a direction of flow as indicated.

0.01 millimolar (mM) phosphate buffer (pH 6.04) was used as the washing solution in the examples.

*Staphylococcus aureus*, used as a template, was amplified through a PCR amplification to obtain the PCR product used in the examples. The base sequence of the SEQ. ID NO. 1 forward primer was 5'-(TAG CAT ATC AGA AGG CAC ACC C)-3', and the base sequence of the SEQ. ID NO. 2 reverse primer was 5'-(ATC CAC TCA AGA GAG ACA ACA TT)-3'. The amplified PCR product had a size of 240 base pairs (bp), the pH of the phosphate buffer including the PCR product was 6.47 and the concentration of the PCR product was 10 nanograms/microliter (ng/μl).

Figure 3B:
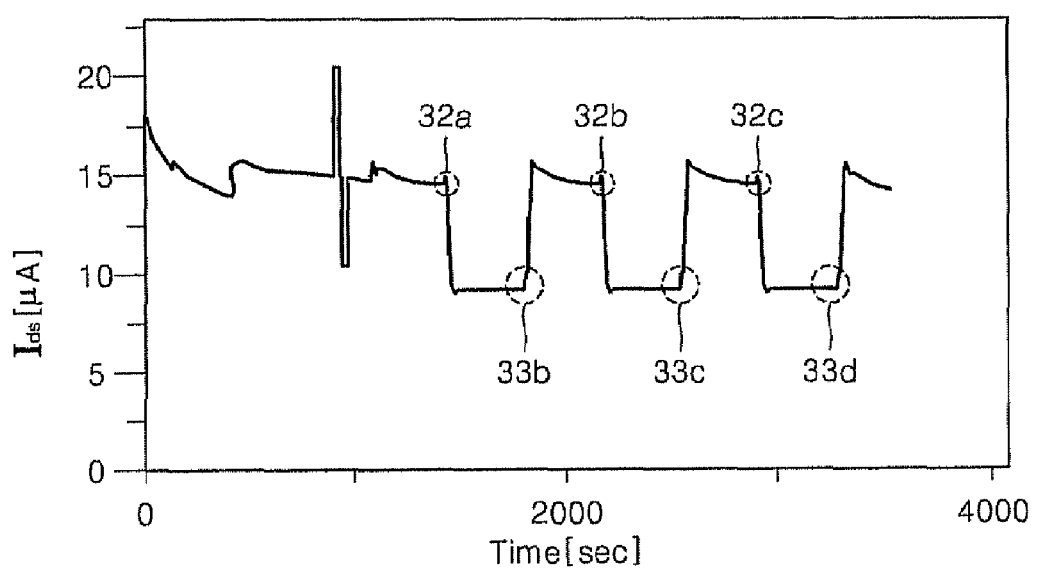
FIG. 3B is a graph illustrating a change in current (Ids) when the PCR products and the washing buffer are alternately provided to the gate electrode of the field effect transistor as shown in FIG. 3A.

FIG. 3B is a graph illustrating a change in current ($I_{ds}$) when the PCR products and the washing buffer were alternately provided to the gate electrode of the field effect transistor as shown in FIG. 3A.

Referring to FIG. 3B, the current ($I_{ds}$) rapidly decreased when the PCR products (32a, 32b and 32c) were provided. On the other hand, the current ($I_{ds}$) rapidly increased when the washing solutions (33b, 33c and 33d) were provided.

The obtained current change was converted into surface voltage change. The results of the surface voltage change are shown in Table 1 below.

TABLE 1

| Providing PCR product | | Providing washing solution | |
|---|---|---|---|
| 32a | Decrease by 88.59 mV | 33b | Increase by 90.14 mV |
| 32b | Decrease by 83.34 mV | 33c | Increase by 90.54 mV |
| 32c | Decrease by 78.06 mV | 33d | Increase by 84.83 mV |

As shown in Table 1, when the PCR product was provided, the voltage of the field effect transistor significantly decreased, and when the washing solution was provided, the voltage of the field effect transistor significantly increased.

It was measured whether the pH difference between the PCR product and the washing solution influenced the voltage. The pH difference between the PCR product and the washing solution was 0.43, and the voltage change due to the pH difference was merely 10 mV. Thus, it was determined that the pH difference does not have a significant influence on the voltage.

Accordingly, a plurality of bio-molecules can be continuously, easily and accurately detected through the exemplary method of detecting the presence of target bio-molecules or a concentration of the target bio-molecules using a field effect transistor without fixing probe bio-molecules according to the present invention. The field effect transistor can be semi-permanently used to detect the target bio-molecules by washing the field effect transistor.

In the exemplary method of detecting the target bio-molecules according to the present invention, various target bio-molecules can be continuously detected using the field effect transistor. The field effect transistor can also be used repeatedly and disposal thereof after a single use is not required. The target bio-molecules can be quickly detected using the field effect transistor in an exemplary method according to the present invention. In addition, since the probe bio-molecules are not fixed on the field effect transistor, the field effect transistor can be simply manufactured and variances of characteristics between a plurality of field effect transistors caused by additional processing can be effectively reduced, and thus the target bio-molecules can be accurately detected.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. A method of detecting a presence of target bio-molecules or a concentration of the target bio-molecules using a field effect transistor, the method comprising:
    allowing a first sample including a first target bio-molecule to contact a sensing surface of the field effect transistor;
    flowing the first sample including the first target bio-molecule across the sensing surface of the field effect transistor without binding the first target bio-molecule to a fixed position;
    measuring a change in an electric signal of the field effect transistor, the field effect transistor comprising:
        a substrate,
        a source region; and
        a drain region,
            wherein the source region and the drain region are formed apart from each other on the substrate, and the source region and the drain region are each doped having an opposite polarity than a polarity of the substrate, and wherein a channel region is disposed between the source region and the drain region and an insulating layer is disposed on the channel region and includes the sensing surface, and determining a presence of the first target bio-molecule using the measured change in the electric signal of the field effect transistor, wherein changes in the electrical signal resulting from a change in pH due to the flowing of the first sample are disregarded in the determining of the presence of the first target bio-molecule.

2. The method of claim 1, wherein the substrate of the field effect transistor is formed of a semiconductor material.

3. The method of claim 1, wherein the insulating layer is composed of an electrically insulating material.

4. The method of claim 1, further comprising allowing a second sample including a second target bio-molecule to contact the sensing surface of the field effect transistor.

5. The method of claim 4, further comprising washing the sensing surface of the field effect transistor with a solution which lacks bio-molecules before the allowing the second sample including the second target bio-molecule to contact the sensing surface of the field effect transistor.

6. The method of claim 1, wherein the electric signal is at least one selected from the group consisting of a drain current, a gate-source voltage, and a source-drain voltage.

7. The method of claim 1, wherein the bio-molecules include at least one of a nucleic acid and a protein.

8. The method of claim 7, wherein the nucleic acid is selected from the group consisting of deoxyribonucleic acid (DNA), ribonucleic acid (RNA), peptide nucleic acid (PNA), locked nucleic acid (LNA) and a hybrid thereof.

9. The method of claim 7, wherein the protein is selected from the group consisting of an enzyme, a substrate, an antigen, an antibody, a ligand, an aptamer, and a receptor.

10. The method of claim 7, wherein the nucleic acid is a polymerase chain reaction (PCR) product or a purified polymerase chain reaction (PCR) product.

11. The method of claim 1, wherein the substrate is silicon and the electrically insulating material is selected from the group consisting of a silicon dioxide, a silicon nitride, and a metal oxide.

12. The method of claim 1, wherein the field effect transistor is at least partially formed in a microchannel.

13. The method of claim 1, wherein the field effect transistor is in fluid communication with a microchannel.

14. The method of claim 13, wherein an inner wall of the microchannel is comprised of the substrate.

15. The method of claim 1, further comprising forming an additional insulating layer disposed on the insulating layer, wherein the additional layer is composed of a separate material selected to prevent binding with target biomolecules.

16. The method of claim 5, wherein the field effect transistor is configured such that a pH difference between the first sample including the first target biomolecule and the solution which lacks biomolecules is responsible for less than half of the measured change in the electric signal of the field effect transistor.

* * * * *